(12) United States Patent
Schommer

(10) Patent No.: US 7,482,783 B2
(45) Date of Patent: Jan. 27, 2009

(54) SHIPPING CONTAINER FOR AN IMPLANTABLE MEDICAL DEVICE

(75) Inventor: Mark E Schommer, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 263 days.

(21) Appl. No.: 11/429,846

(22) Filed: May 8, 2006

(65) Prior Publication Data
US 2006/0197494 A1    Sep. 7, 2006

Related U.S. Application Data

(62) Division of application No. 10/836,312, filed on Apr. 30, 2004, now Pat. No. 7,308,316.

(60) Provisional application No. 60/508,199, filed on Oct. 2, 2003.

(51) Int. Cl.
*H01M 10/46* (2006.01)

(52) U.S. Cl. ...................................... 320/108

(58) Field of Classification Search ................ 320/107, 320/108, 109, 112, 114, 115
See application file for complete search history.

(56) References Cited

U.S. PATENT DOCUMENTS

| | | | |
|---|---|---|---|
| 3,842,724 A | 10/1974 | Korr et al. |
| 3,888,260 A | 6/1975 | Fischell |
| 4,041,955 A | 8/1977 | Kelly et al. |
| 4,134,408 A | 1/1979 | Brownlee et al. |
| 5,279,292 A | 1/1994 | Baumann et al. |
| 5,314,453 A | 5/1994 | Jeutter |
| 5,314,457 A | 5/1994 | Jeutter et al. |
| 5,314,458 A | 5/1994 | Najifi et al. |
| 5,370,666 A | 12/1994 | Lindberg et al. |
| 5,396,985 A | 3/1995 | Seki |
| 5,411,537 A | 5/1995 | Munshi et al. |
| 5,522,856 A | 6/1996 | Reineman |

(Continued)

FOREIGN PATENT DOCUMENTS

WO    WO 98/08567    3/1998

(Continued)

OTHER PUBLICATIONS

International Search Report from International Application No. PCT/US2004/030129.

*Primary Examiner*—Edward Tso
(74) *Attorney, Agent, or Firm*—William D. Bauer; Beth L. McMahon

(57) ABSTRACT

Shipping container for an implantable medical device having a secondary coil operatively coupled to therapeutic componentry. The container is configured to hold the implantable medical device in the container with the secondary coil positioned within a distance of a first face allowing charging of the implantable medical device without disturbing the container. The container has indicia representative of a lateral location on the first face aligned with the secondary coil of the implantable medical device. Thus, the indicia may be utilized to place an external antenna in order to charge the implantable medical device without disturbing the container. Alternatively, instead of using indicia, the implantable medical device is located in a predetermined position within the container so that the external antenna may be place with respect to the predetermined position in order to charge the implantable medical device without disturbing the container.

21 Claims, 7 Drawing Sheets

U.S. PATENT DOCUMENTS

| | | | |
|---|---|---|---|
| 5,613,935 A | 3/1997 | Jarvik | |
| 5,702,431 A | 12/1997 | Wang et al. | |
| 5,713,939 A | 2/1998 | Nedungadi et al. | |
| 5,733,313 A | 3/1998 | Barreras, Sr. et al. | |
| 5,749,909 A | 5/1998 | Schroeppel et al. | |
| 5,948,006 A | 9/1999 | Mann | |
| 5,991,665 A | 11/1999 | Wang et al. | |
| 6,067,474 A | 5/2000 | Schulman et al. | |
| 6,154,677 A | 11/2000 | Leysieffer | |
| 6,178,353 B1 | 1/2001 | Griffith et al. | |
| 6,275,737 B1 | 8/2001 | Mann | |
| 6,478,030 B1 | 11/2002 | Shapeton et al. | |
| 6,551,345 B2 | 4/2003 | Vogel et al. | |
| 6,687,543 B1 | 2/2004 | Isaac et al. | |
| 6,727,814 B2 | 4/2004 | Saltzstein et al. | |
| 2002/0161402 A1 | 10/2002 | Vogel et al. | |
| 2003/0058097 A1 | 3/2003 | Saltzstein et al. | |
| 2003/0195566 A1 | 10/2003 | Vogel et al. | |
| 2003/0204218 A1 | 10/2003 | Vogel et al. | |

FOREIGN PATENT DOCUMENTS

| | | |
|---|---|---|
| WO | WO 98/37926 | 9/1998 |
| WO | WO 99/06108 | 2/1999 |
| WO | WO 99/44684 | 9/1999 |
| WO | WO 00/01442 | 1/2000 |
| WO | WO 01/97908 | 12/2001 |
| WO | WO 02/087686 | 11/2002 |

SHIPPING CONTAINER FOR AN IMPLANTABLE MEDICAL DEVICE

RELATED APPLICATION

This application claims priority from provisional U.S. Application Ser. No. 60/508,199, filed Oct. 2, 2003, and from U.S. application Ser. No. 10/836,312, filed Apr. 30, 2004, which are hereby incorporated by reference in their entirety

FIELD OF THE INVENTION

This invention relates to implantable medical devices and, in particular, shipping containers for such implantable medical devices.

This invention relates to shipping containers and, in particular, to shipping containers for implantable medical devices.

BACKGROUND OF THE INVENTION

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators and cochlear implants. Of course, it is recognized that other implantable medical devices are envisioned which utilize energy delivered or transferred from an external device.

A common element in most of these implantable medical devices is the need for electrical power in the implanted medical device. The implanted medical device typically requires electrical power to perform its therapeutic function whether it be driving an electrical infusion pump, providing an electrical neurostimulation pulse or providing an electrical cardiac stimulation pulse. This electrical power is derived from a power source.

Typically, a power source for an implantable medical device is a rechargeable power source such as rechargeable batteries and, in particular, lithium ion batteries. Such batteries can have a capacity which is exhausted much earlier than the useful life of the implantable medical device. Electrical power can be transcutaneously transferred to the implanted medical device to recharge temporarily positioned on the surface of the skin of the patient can recharge the implanted medical device's batteries. In fact, many systems and methods have been used for transcutaneously inductively recharging a rechargeable power source used in an implantable medical device.

Transcutaneous energy transfer through the use of inductive coupling involves the placement of two coils positioned in close proximity to each other on opposite sides of the cutaneous boundary. The internal coil, or secondary coil, is part of or otherwise electrically associated with the implanted medical device. The external coil, or primary coil, is associated with the external power source or external charger, or recharger. The primary coil is driven with an alternating current. A current is induced in the secondary coil through inductive coupling. This current can then be used to charge, or recharge, an internal power source.

BRIEF SUMMARY OF THE INVENTION

Implantable medical devices are commonly shipped from the manufacturer to a medical facility where implantation of the device is performed. It is preferable that the implantable medical device not be in a fully charged state following manufacture and during shipment, storage and ultimately use. Ultimate battery life can be improved if the implantable medical device is not fully charged when shipped. Typically, an implantable medical device can be far from a fully charged and typically about eighty percent (80%) charged when shipped.

However, implanting an implantable medical device without a full charge is not desirable. Soon after implantation, it is generally desirable for the newly implanted medical device to be programmed, if necessary, utilized while initially implanted in the patient and monitored by medical personnel soon.

As noted above, inductive charging of the implanted medical device usually requires placing an external antenna directly on the skin of the patient at the site of implantation. However, the implantation site will typically still be recovering from the trauma of implantation immediately or soon after implantation. The implantation site can be adversely affected by the external charging unit if charging of the newly implanted medical device is attempted. Therefore, it is desirable to put off charging a newly implanted medical device for as long as possible, or typically one full charge period of the implanted medical device.

Contrary to conventional shipping techniques designed to ensure maximum battery life, it is desirable for an implantable medical device to be fully charged at the time of implantation. This will allow a maximum amount of time for the implantation site to heal before transcutaneous charging is attempted.

During shipment and storage, an implantable medical device is usually contained in a sterile environment in a storage container, such as a box. This would help to prevent contamination of the implantable medical device with germs, for example, and would help prevent subsequent infection of the patient upon implantation. Removal of the implantable medical device from the sterile environment of the shipping and/or storage container could subject the implantable medical device to the risk of contamination.

However, as noted above, charging of implantable medical device usually requires very close placement of an external antenna to the secondary coil of the implantable medical device in order to achieve effective inductive coupling. Such close placement is extremely difficult with the implantable medical device contained in the sterile environment of the shipping and/or storage container.

Thus, medical practitioners are often faced with a dilemma of removing the implantable medical device from the sterile environment of the container and being able to implant a fully charged medical device, or ensuring that the implantable medical device remains sterile but only being able to implant a partially charged medical device which could limit early use of the medical device or subject the already traumatized implantation site to the additional trauma of an external antenna soon after implantation.

In an embodiment, the present invention provides a shipping container for an implantable medical device having a secondary coil operatively coupled to therapeutic componentry. A container for holding the implantable medical device has a first face. The container is configured to hold the implantable medical device in the container with the secondary coil positioned within a distance of the first face allowing charging of the implantable medical device without disturbing the container. The container has indicia representative of a lateral location on the first face aligned with the secondary coil of the implantable medical device. Thus, the indicia may be utilized to place an external antenna in order to charge the implantable medical device without disturbing the container.

In an embodiment, a center of the secondary coil and the indicia are centered on the first face of the container.

In an embodiment, the indicia is placed on the first face of the container.

In an embodiment, the indicia is placed on at least one face of the container adjacent to the first face.

In an embodiment, the indicia is placed on a plurality of faces of the container adjacent to the first face.

In an embodiment, an interior of the container holding the implantable medical device is sterile.

In an embodiment, the container is an internal container contained within an outer container.

In an embodiment, the indicia is positioned inside an outer layer of the container and with at least a portion of the outer container covering at least a portion of the indicia being transparent.

In an embodiment, the indicia is represented by the implantable medical device and transparency of at least a portion of the first face of the container.

In an embodiment, the present invention provides a shipping, container for an implantable medical device having a secondary coil operatively coupled to therapeutic componentry. A container holds the implantable medical device with the secondary coil positioned within a distance of the first face allowing charging of the implantable medical device without disturbing the container. The implantable medical device is located in a predetermined position within the container. Thus, an external antenna may be placed with respect to the predetermined position in order to charge the implantable medical device without disturbing the container.

In an embodiment, the predetermined position results in the secondary coil being laterally centered on the first face of the container.

DETAILED DESCRIPTION OF THE INVENTION

Figure 1:
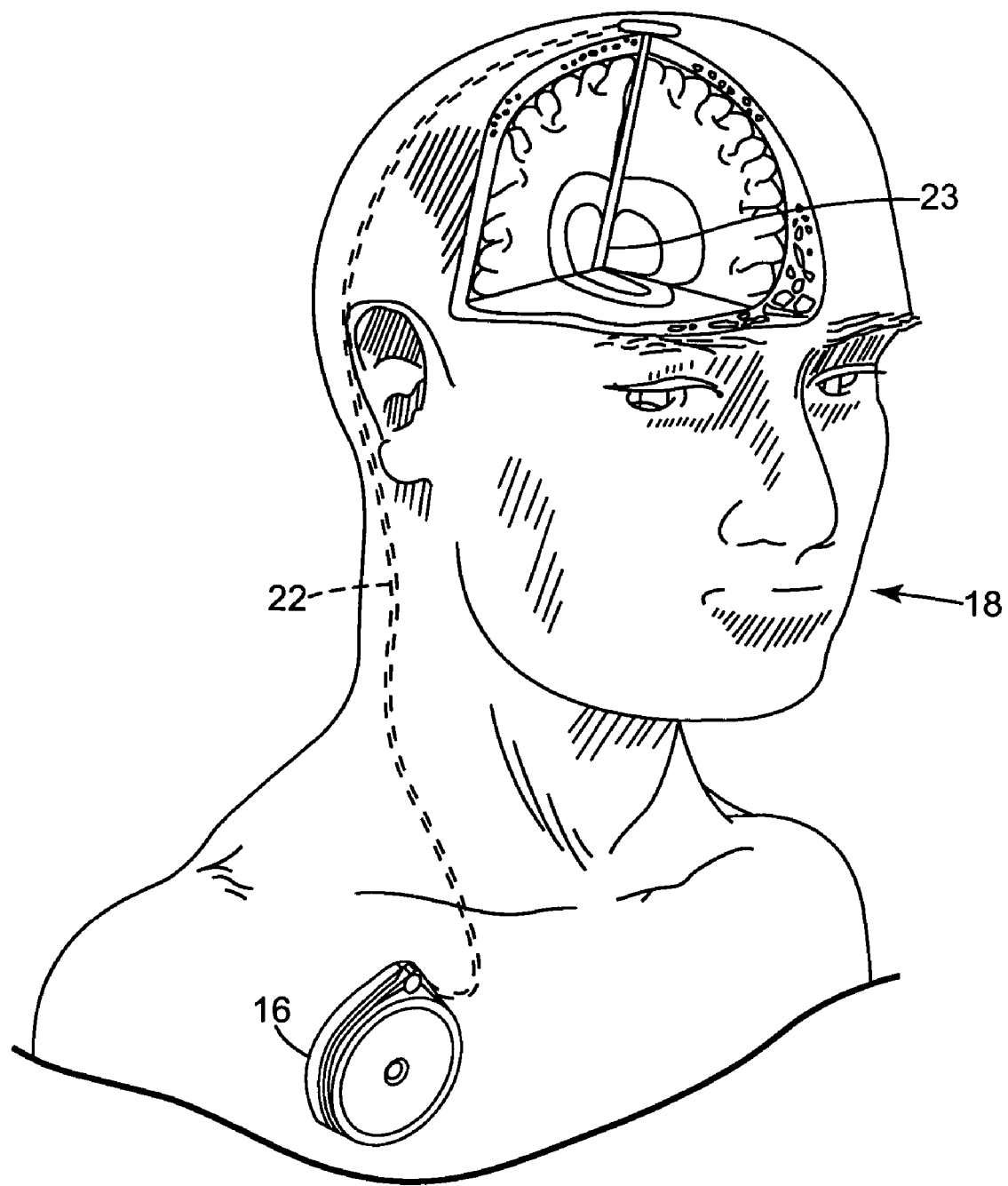
FIG. 1 illustrates an implantable medical device implanted in a patient.

FIG. 1 shows implantable medical device 16, for example, a drug pump, implanted in patient 18. The implantable medical device 16 is typically implanted by a surgeon in a sterile surgical procedure performed under local, regional, or general anesthesia. Before implanting the medical device 16, a catheter 22 is typically implanted with the distal end position at a desired therapeutic delivery site 23 and the proximal end tunneled under the skin to the location where the medical device 16 is to be implanted. Implantable medical device 16 is generally implanted subcutaneously at depths, depending upon application and device 16, of from 1 centimeter (0.4 inches) to 2.5 centimeters (1 inch) where there is sufficient tissue to support the implanted system. Once medical device 16 is implanted into the patient 18, the incision can be sutured closed and medical device 16 can begin operation.

Implantable medical device 16 operates to infuse a therapeutic substance into patient 18. Implantable medical device 16 can be used for a wide variety of therapies such as pain, spasticity, cancer, and many other medical conditions.

The therapeutic substance contained in implantable medical device 16 is a substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances may or may not be intended to have a therapeutic effect and are not easily classified such as saline solution, fluoroscopy agents, disease diagnostic agents and the like. Unless otherwise noted in the following paragraphs, a drug is synonymous with any therapeutic, diagnostic, or other substance that is delivered by the implantable infusion device.

Implantable medical device 16 can be any of a number of medical devices such as an implantable therapeutic substance delivery device, implantable drug pump, cardiac pacemaker, cardioverter or defibrillator, as examples.

Figure 2:
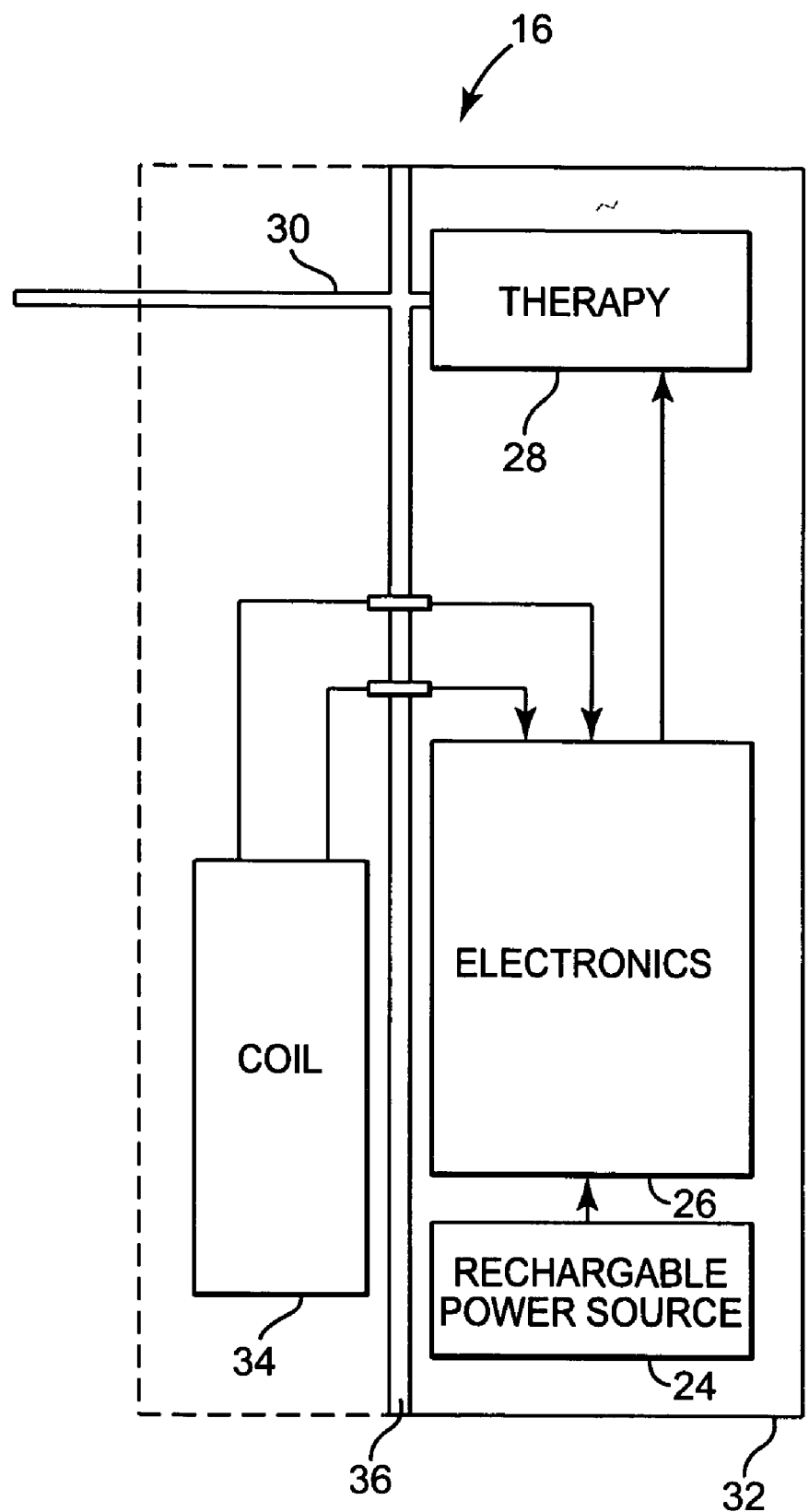
FIG. 2 is a block diagram of an implantable medical device.

In FIG. 2, implantable medical device 16 has a rechargeable power source 24, such as a Lithium ion battery, powering electronics 26 and therapy module 28 in a conventional manner. Therapy module 28 is coupled to patient 18 through one or more therapy connections 30, also conventionally. Rechargeable power source 24, electronics 26 and therapy module 28 are contained in hermetically sealed housing 32. Secondary charging coil 34 is attached to the exterior of housing 32. Secondary charging coil 34 is operatively coupled through electronics 26 to rechargeable power source 24. In the alternative, secondary charging coil 34 could be contained in housing 32 or could be contained in a separate housing umbilically connected to electronics 26. Electronics 26 help provide control of the charging rate of rechargeable power source 24 in a conventional manner. Magnetic shield 36 is positioned between secondary charging coil 34 and housing 32 in order to protect rechargeable power source 24, electronics 26 and therapy module 28 from electromagnetic energy when secondary charging coil 34 is utilized to charge rechargeable power source 24.

Rechargeable power source 24 can be any of a variety power sources including a chemically based battery or a capacitor. Rechargeable power source can be a well known lithium ion battery.

Figure 3:
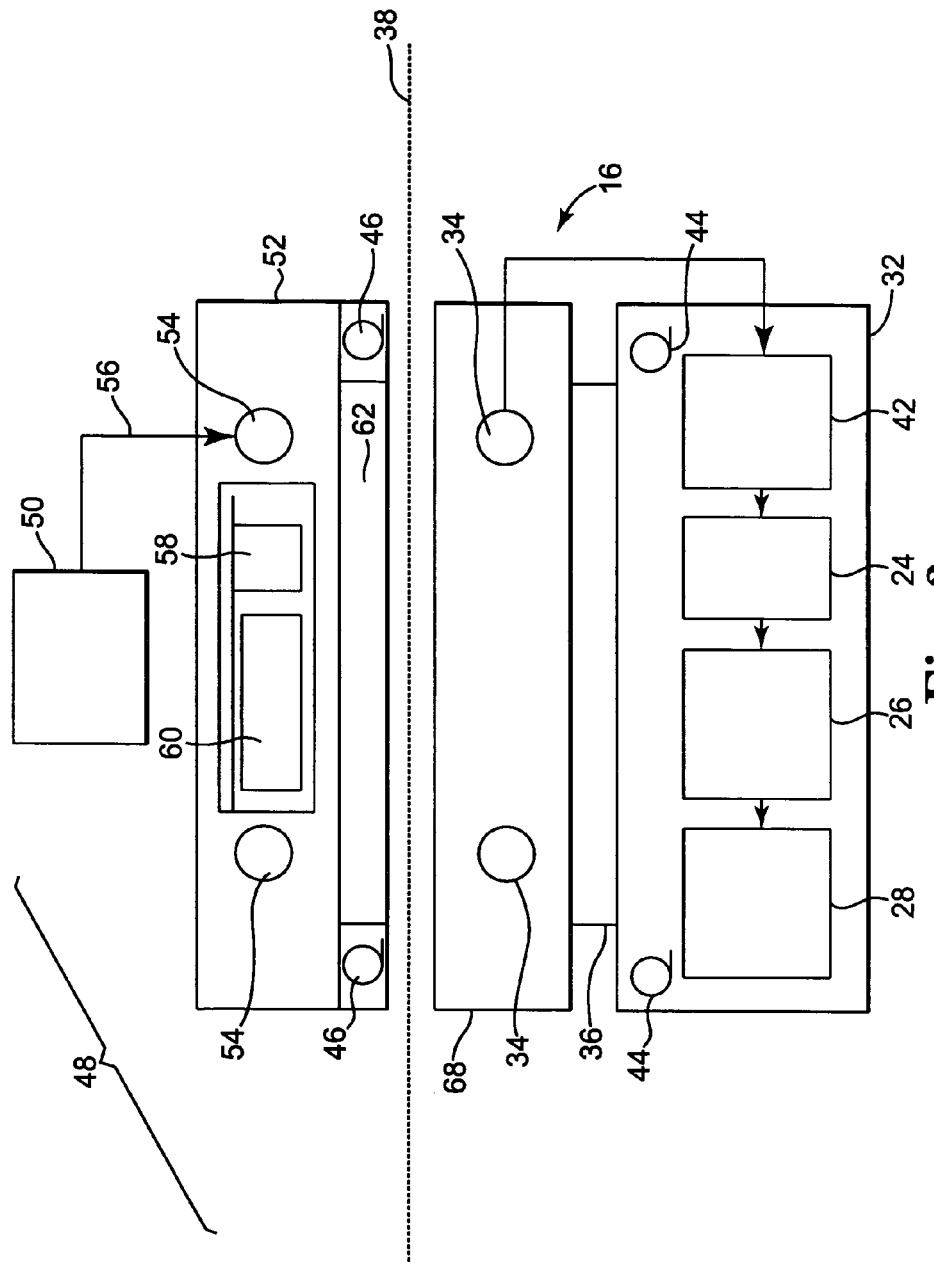
FIG. 3 is a detailed block diagram of an implantable medical device implanted subcutaneously and an associated external charging device.

FIG. 3 illustrates an alternative of implantable medical device 16 situated under cutaneous boundary 38. Implantable medical device 16 is similar to the device illustrated in FIG. 2. However, charging regulation module 42 is shown separate from electronics 26 controlling therapy module 28. Again, charging regulation and therapy control is conventional.

Implantable medical device 16 also has internal telemetry coil 44 configured in conventional manner to communicate through external telemetry coil 46 to an external programming device (not shown), charging unit 50 or other device in a conventional manner in order to both program and control implantable medical device and to externally obtain information from implantable medical device 16 once implantable medical device has been implanted. Internal telemetry coil 44, rectangular in shape with dimensions of 1.85 inches (4.7 centimeters) by 1.89 inches (4.8 centimeters) constructed from 150 turns of 43 AWG wire, is sized to be larger than the diameter of secondary charging coil 34. Secondary coil 34 is constructed with 182 turns of 30 AWG wire with an inside diameter of 0.72 inches (1.83 centimeters) and an outside diameter of 1.43 inches (3.63 centimeters) with a height of 0.075 inches (0.19 centimeters). Magnetic shield 36 is positioned between secondary charging coil 34 and housing 32 and sized to cover the footprint of secondary charging coil 34.

Internal telemetry coil 44, having a larger diameter than secondary coil 34, is not completely covered by magnetic shield 36 allowing implantable medical device 16 to communicate with the external programming device with internal telemetry coil 44 in spite of the presence of magnetic shield 36.

Rechargeable power source 24 can be charged while implantable medical device 16 is in place in a patient through the use of external charging device 48. External charging device 48 may consist of charging unit 50 and external antenna 52. Charging unit 50 contains the electronics necessary to drive primary coil 54 with an oscillating current in order to induce current in secondary coil 34 when primary coil 54 is placed in the proximity of secondary coil 34. Charging unit 50 is operatively coupled to primary coil by cable 56. Charging unit 50 and antenna 52 may be combined into a single unit. Antenna 52 may also optionally contain external telemetry coil 46 which may be operatively coupled to charging unit 50 if it is desired to communicate to or from implantable medical device 16 with external charging device 48. Alternatively, antenna 52 may optionally contain external telemetry coil 46 which can be operatively coupled to an external programming device, either individually or together with external charging unit 48.

Figure 4:
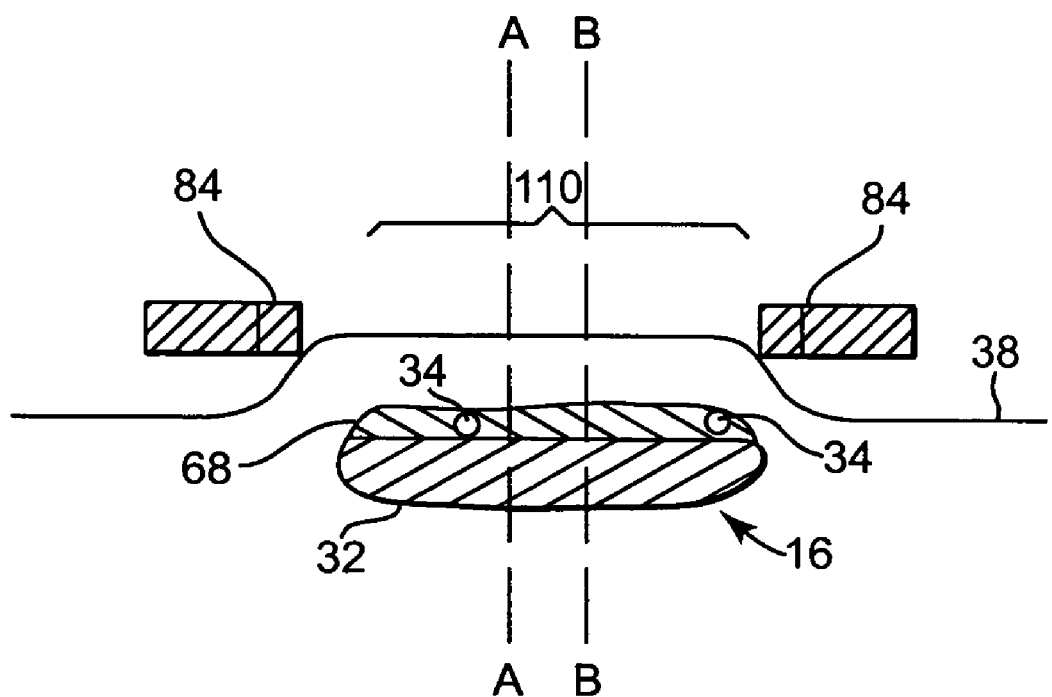
FIG. 4 is a cross-sectional side view of an implantable medical device implanted subcutaneously and an associated bracket for use with an external antenna.

FIG. 4 is cross-sectional view of implantable medical device 16 implanted in patient 18 approximately one centimeter under cutaneous boundary 38 creating bulging area 110, an area of the body of patient 18 in which the skin of patient 18 is caused to bulge slightly due to the implantation of implantable medical device 16. Bulging area 110 is an aid to locating the position of external antenna 52 relative to secondary coil 34. Bracket 84 can be positioned roughly in the area where implantable medical device 16 is implanted. Opening 108 in bracket 84 can aid is establishing the location of implantable medical device. Bracket 84 can be roughly centered over bulging area 110. After external antenna 52 is coupled to bracket 84, then primary coil 54 can be generally centered on implantable medical device 16.

However, secondary coil 34 may not be centered with respect to implantable medical device 16. This can occur due to a variety of reasons such as the need for operatively coupling secondary coil 34 to charging regulation module 42. Connections to make this operative coupling may require physical space on one side of internal antenna 68 which may cause secondary coil 34 not to be centered on implantable medical device 16. It is also possible that the attachment of internal antenna 68 to housing 32 can cause secondary coil 34 not to be centered on implantable medical device 16. Regardless of the cause, if secondary coil 34 is not centered on implantable medical device 16, then centering bracket 84 on bulging area 110 may not optimally position primary coil 54 with respect to secondary coil 34. Any offset in the position of primary coil 54 and secondary coil 34 may not result in the most efficient energy transfer from external antenna 52 to implantable medical device 16.

Inductive coupling between primary coil 54 of external antenna 52 and secondary coil of implantable medical device 16 is accomplished at a drive, or carrier, frequency, $f_{carrier}$, in the range of from eight (8) to twelve (12) kiloHertz. The carrier frequency $f_{carrier}$, of external antenna 54 is approximately nine (9) kiloHertz unloaded.

Figure 5:
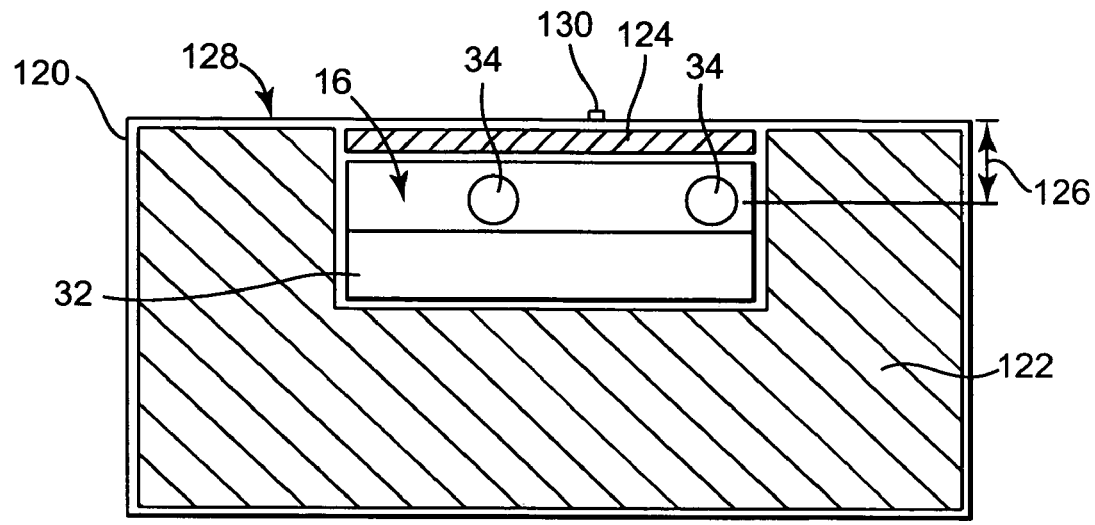
FIG. 5 is a cross-section of a container holding implantable medical device.

However, implantable medical device 16 is shipped to the implantation location and, possibly, stored before implantable medical device 16 can be implanted into patient 16. An embodiment (see FIG. 5) allows implantable medical device 16 to be shipped, and possibly, stored in a partially charged state, or even a completely discharged state. Container 120 holds implantable medical device 16 securely utilizing packing material 122 and 124. Implantable medical device 16 is positioned with secondary coil 34 located distance 126 away from one face 128 of container 120. Distance 126 is selected such that implantable medical device 16 can be charged using external antenna 52 positioned near or against face 128 on container 120 without opening the sterile portion of container 120 or removing implantable medical device 16 from container 120. Distance 126 may have the same guidelines as the distance implantable medical device 16 is implanted below the skin surface, or from 1 centimeter (0.4 inches) to 2.5 centimeters (1 inch). Of course, distance 126 could be greater or less than these dimensions depending upon charging requirements and cushioning requirements. Generally, charging conditions in container 120 are not as stringent as charging conditions in an implanted condition so, in appropriate circumstances, the requirements on distance 126 may be relaxed.

Figure 6:
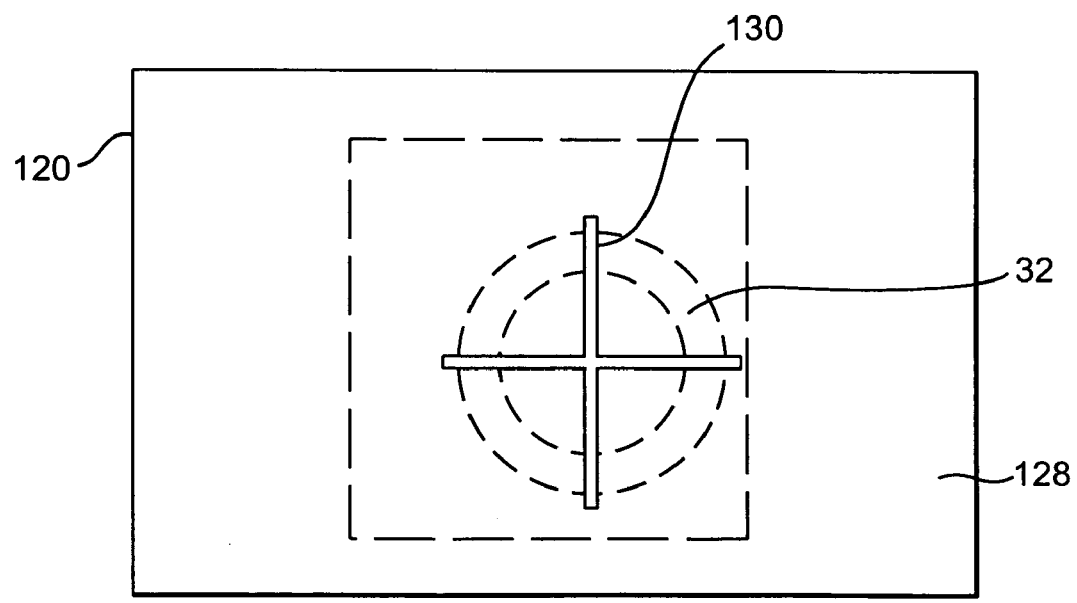
FIG. 6 is a top view of the container illustrated in FIG. 5.

As shown in FIG. 4, secondary coil 34 is not centered on implantable medical device 16. In FIG. 6 indicia 130 on face 128 of container 120 is indicative of the center of secondary coil 34 (shown by dashed lines although not visible in FIG. 6). Indicia 130 may be any marking which would indicate the approximate laterally centered location of secondary coil 34 on face 128. Indicia 130 is shown as cross hairs but may also be any other suitable indicia, as for example, a bulls eye or outline or shadow of antenna 52. Indicia 130 may be applied to face 128 or may be formed into face 128, painted or marked on face 128. Indicia 130 may appear separate or may be incorporated into other markings or designs on face 128. It is also possible that indicia 128 is not actually on face 128 but could be located on adjacent sides of container 120, for example, but still giving an indication of the approximate lateral (to face 128) location of secondary coil 34. It is only important that indicia 130 be visible enough to allow a user to properly located external antenna 52 in order to charge implantable medical device 16.

Figure 7:
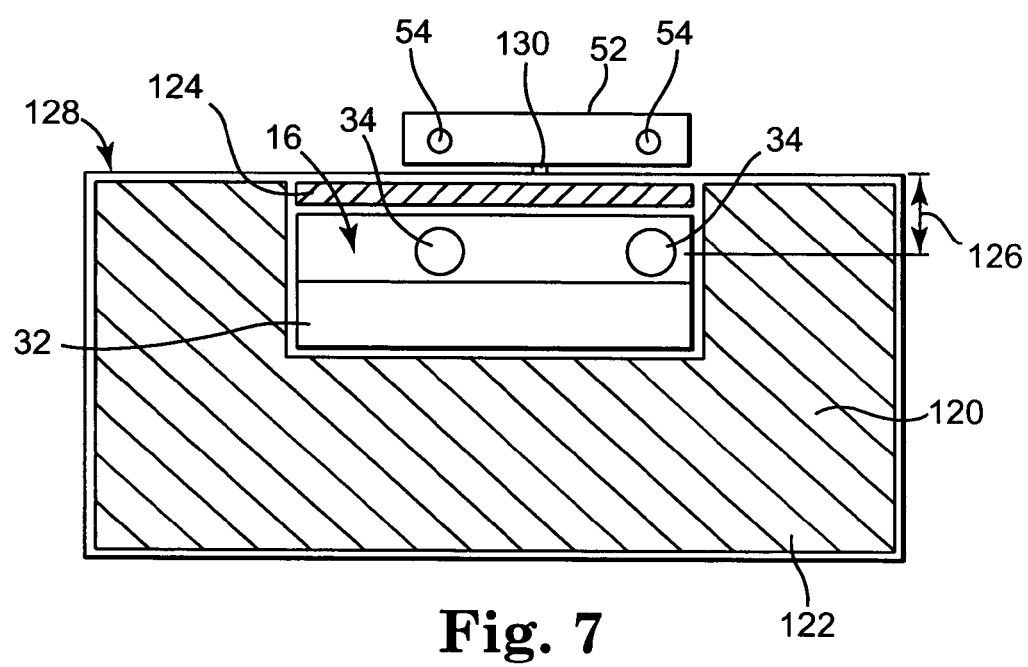
FIG. 7 is a cross-section similar to FIG. 5 with external antenna positioned to charge implantable medical device.

FIG. 7 illustrates container 120 holding implantable medical device 16 with external antenna 52 containing primary coil 54 properly positioned with respect to indicia 130 on, or near, face 128 to be able to properly charge implantable medical device 16 without disturbing the sterile environment of implantable medical device 16.

Figure 8:
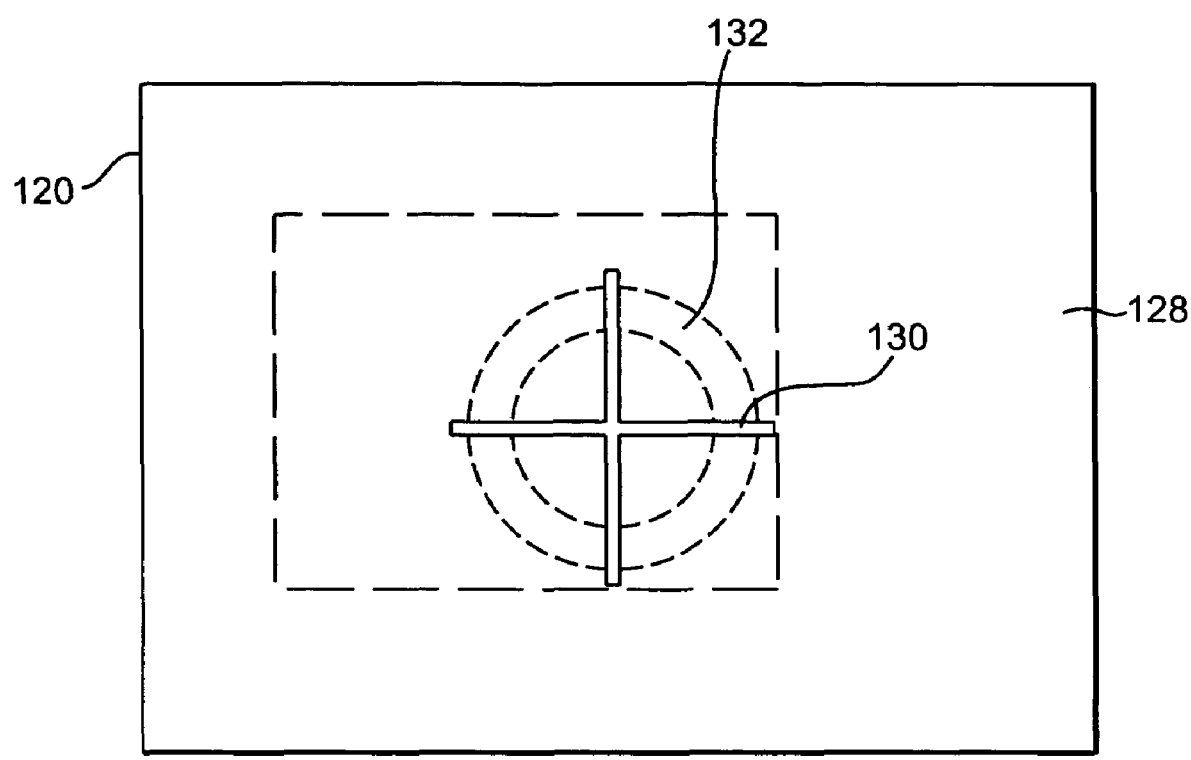
FIG. 8 illustrates an alternative with the charging location centered on the face of the container.

The center of indicia 130, i.e., the indication of the center of secondary coil 34, may be nearly exactly the center of face 128 of container 120 as shown in FIG. 8. Making the center of indicia 130 also the center of face 128 eliminates the possibility of misalignment if a box lid is attached incorrectly to the rest of container, for example.

Alternatively, with implantable medical device 16 having been located in a predetermined position within container 120, e.g., with secondary coil 34 laterally centered on face 128, indicia 130 may be completely omitted. Knowing that secondary coil 34 is centered on face 128 of container 120, external antenna 52 may simply be positioned laterally centered on face 128 of container 120, i.e., matching the predetermined location of implantable medical device 16, and secondary will be properly positioned for charging. In this alternative, indicia 130 in FIG. 8 would be eliminated.

Although implantable medical device 16 has been illustrated as being held in a single container 120, it is to be recognized and understood that other configurations are possible and contemplated to be within the scope of the present invention. For example, implantable medical device 16 could be contained in a smaller, sterile container which in turn is shipped in a larger container providing, for example, cushioned during shipment. Implantable medical device 16 could still be charged by opening the larger container without disturbing the sterile container and charging implantable medical device 16 therein. In this case, indicia 130 could be represented on either the larger container, the smaller container or some combination as long as external antenna can be properly located for charging.

It is also contemplated that other, non-standard forms of indicia 130 could be utilized. For example, sterile container 120, or a sub-container, could be transparent and indicia 130 could be located within container 120, or sub-container, and could even be implantable medical device 16 itself or evidenced on implantable medical device 16.

It is recognized that implantable medical device 16 could be shipped or stored fully discharged, partially charged or essentially fully charged. Charging, full or partial, could still be desired, as for example, topping off the charge of implantable medical device 16 before implantation.

It is also recognized and understood that secondary coil 34 could be separate from, completely apart from or only semi-attached to the remainder of implantable medical device 16. In this case, the positioning and indicia 130 would still apply to the portion of the apparatus or assembly containing secondary coil 34 or to secondary coil 34 separately.

Thus, embodiments of the shipping container for an implantable medical device are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A shipping container for an implantable medical device having a secondary coil operatively coupled to therapeutic componentry, comprising:
    a container for holding said implantable medical device, said container having a first face;
    said container configured to hold said implantable medical device in said container with said secondary coil positioned within a distance of said first face;
    said distance allowing charging of said implantable medical device without disturbing said container;
    said container having indicia representative of a lateral location on said first face aligned with said secondary coil of said implantable medical device;
    whereby said indicia may be utilized to place an external antenna in order to charge said implantable medical device without disturbing said container.

2. A shipping container as in claim 1 wherein a center of said secondary coil and said indicia are centered on said first face of said container.

3. A shipping container as in claim 1 wherein said indicia is placed on said first face of said container.

4. A shipping container as in claim 1 wherein said indicia is placed on at least one face of said container adjacent to said first face.

5. A shipping container as in claim 1 wherein said indicia is placed on a plurality of faces of said container adjacent to said first face.

6. A shipping container as in claim 1 wherein said indicia comprises cross hairs.

7. A shipping container as in claim 1 wherein said indicia comprises circular indicia.

8. A shipping container as in claim 1 wherein said indicia comprises concentric circles.

9. A shipping container as in claim 8 wherein said indicia comprises a bulls eye.

10. A shipping container as in claim 1 wherein said indicia comprises a shadow of said secondary antenna.

11. A shipping container as in claim 1 wherein an interior of said container holding said implantable medical device is sterile.

12. A shipping container as in claim 1 wherein said distance is not more than five (5) centimeters.

13. A shipping container as in claim 12 wherein said distance is not more than two and one half (2½) centimeters.

14. A shipping container as in claim 13 wherein said distance is approximately one (1) centimeter.

15. A shipping container as in claim 1 wherein said container is an internal container contained within an outer container.

16. A shipping container as in claim 15 wherein said outer container is a shipping container providing cushioning for said implantable medical device.

17. A shipping container as in claim 15 wherein said indicia is positioned on said outer container.

18. A shipping container as in claim 1 wherein said indicia is positioned inside an outer layer of said container and with at least a portion of said outer container covering at least a portion of said indicia being transparent.

19. A shipping container as in claim 1 wherein said indicia is represented by said implantable medical device and transparency of at least a portion of said first face of said container.

20. A shipping container for an implantable medical device having a secondary coil operatively coupled to therapeutic componentry, comprising:
    a container for holding said implantable medical device, said container having a first face;
    said container configured to hold said implantable medical device in said container with said secondary coil positioned within a distance of said first face;
    said distance allowing charging of said implantable medical device without disturbing said container;
    said secondary coil of said implantable medical device being located in a predetermined lateral position within said container that is designated by indicia on said first face of said container;
    whereby an external antenna may be placed with respect to said predetermined lateral position in order to charge said implantable medical device without disturbing said container.

21. A shipping container as in claim 20 wherein said predetermined position comprises said secondary coil being laterally centered on said first face of said container.

* * * * *